(12) United States Patent
Ishikawa et al.

(10) Patent No.: US 8,331,527 B2
(45) Date of Patent: Dec. 11, 2012

(54) X-RAY CT APPARATUS AND METHOD FOR CORRECTING X-RAY BEAM POSITION

(75) Inventors: Takashi Ishikawa, Tokyo (JP); Keizo Saito, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 263 days.

(21) Appl. No.: 12/919,345

(22) PCT Filed: Mar. 2, 2009

(86) PCT No.: PCT/JP2009/053805
§ 371 (c)(1),
(2), (4) Date: Aug. 25, 2010

(87) PCT Pub. No.: WO2009/110399
PCT Pub. Date: Sep. 11, 2009

(65) Prior Publication Data
US 2011/0007866 A1    Jan. 13, 2011

(30) Foreign Application Priority Data
Mar. 3, 2008    (JP) .................................. 2008-051555

(51) Int. Cl.
*A61B 6/00*    (2006.01)
(52) U.S. Cl. ............................................................ 378/4
(58) Field of Classification Search ................. 378/4–21
See application file for complete search history.

(56) References Cited

FOREIGN PATENT DOCUMENTS

| JP | 5-56958 | 3/1993 |
|---|---|---|
| JP | 7-116157 | 5/1995 |

OTHER PUBLICATIONS

International Search Report in PCT/JP2009/053805, Apr. 21, 2009.

*Primary Examiner* — Courtney Thomas
(74) *Attorney, Agent, or Firm* — Cooper & Dunham LLP

(57) ABSTRACT

An X-ray tube 1 is heated under an X-ray scan condition (tube voltage V, tube current I, exposure time width t) and thus a focal point is shifted. Artifact occurs in a reconstructed image due to the focal point shift. The present invention has an object to enable correction of the focal point shift caused by heating the tube. The applicant and inventor of this application has confirmed that the focal point shift amount of the tube 1 varies in accordance with whether it is in a heating direction or cooling direction when viewed from a past sequence. Therefore, the sequence record and the focal point shift amount based on the heating and cooling directions are stored as data in a storage device 13. A just near past sequence record when viewed from now is stored in a storage unit 16, and the tube temperature is detected by a tube temperature detector 15. On the basis of this temperature and the data in the storage unit 16, heating or cooling and the present accumulated heat capacity are determined in a determining unit 17, and the storage device 13 is accessed to determine a focal point shift amount. The position of the tube is corrected on the basis of this shift amount.

6 Claims, 4 Drawing Sheets

(a)

(b) (ENLARGED VIEW IN BROKEN LINE)

(c) X-RAY EXPOSURE SECTION

X-RAY CT APPARATUS AND METHOD FOR CORRECTING X-RAY BEAM POSITION

TECHNICAL FIELD

The present invention relates to an X-ray CT apparatus for performing shift correction on a slice direction of an X-ray beam.

BACKGROUND ART

According to an X-ray CT apparatus, an X-ray tube for irradiating an examinee with X-ray and an X-ray detector for detecting the dose of X-ray transmitted through the examinee as projection data are rotated around the examinee, a tomographic image of the examinee is reconstructed by using projection data of plural angles detected by the X-ray detector and the reconstructed tomographic image is displayed and supplied for image diagnosis.

The X-ray tube has a cathode for discharging an electron beam and an anode for making the electron beam discharged from the cathode impinge thereto to generate X-ray. The electron beam is accelerated by a high voltage applied between the cathode and the anode, and converted to X-ray in the neighborhood of the surface in the anode when it impinges against the anode. A part of the energy of the accelerated electron beam is converted to X-ray, and most of the remaining part is converted to heat, so that the anode is heated and thermally expanded. As a result, the position on the surface of the anode which substantially serves as an occurrence point of X-ray varies, and thus the position of the X-ray beam varies. The variation of the X-ray occurrence point (also called as X-ray focal point), that is, the variation of the X-ray beam position causes a measurement error of projection data obtained by the X-ray detector and thus causes occurrence of an artifact (false image) on a tomographic image obtained after reconstruction. When an artifact occurs on a tomographic image, the diagnosis performance of the X-ray CT apparatus is remarkably deteriorated and thus it is necessary to correct and reduce the variation of the X-ray occurrence point.

With respect to the conventional correction of the variation amount of the X-ray beam, for example, Patent Document 1 is known. The Patent Document 1 stores the variation amount of X-ray beam due to an accumulated heat capacity in advance, grasps the state of the X-ray tube from the information on the information concerned at the actual measurement time and accumulated heat capacity information at that time point, and corrects the X-ray occurrence point, that is, the X-ray beam position of the X-ray tube.

DISCLOSURE OF THE INVENTION

Problem to be Solved by the Invention

However, it has been difficult to satisfy image quality by correcting the X-ray beam position on the basis of only pre-storage of the focal point shift amount due to the accumulated heat capacity and the accumulated heat capacity at the present time due to heating caused by recent increase of heat capacity of the X-ray tube and increase of the difference in the focal point shift amount under cooling.

An object is to provide an X-ray CT apparatus in which no delay occurs at the time when measurement is prepared, and the center of the X-ray beam is coincident with the center of the X-ray detector immediately after scanning is started without affecting the lifetime of the X-ray tube.

Means of Solving the Problem

According to the present invention, an X-ray CT apparatus having an X-ray tube for generating X-ray with which an examinee is irradiated, and means for obtaining a tomographic image of the examinee by using data of a dose of transmitted X-ray collected by means for collecting X-ray transmitted through the examinee, is characterized by comprising: storage means for storing the relationship between an accumulated heat capacity different between heating and cooling of the X-ray tube and a focal point shift amount in a slice direction; accumulated heat capacity obtaining means for obtaining a present accumulated heat capacity of the X-ray tube; determining means for determining which one of heating and cooling states the X-ray tube is under; and position correcting means for correcting the position of a slice direction of X-ray beam by using a focal point shift amount of the slice direction which is determined on the basis of the accumulated heat capacity obtained by the accumulated heat capacity obtaining means, a determination result of the determining means and the relationship stored in the storage means.

EFFECT OF THE INVENTION

According to the present invention, the measurement can be performed immediately after start of scanning under a state that the center of the slice direction of an X-ray beam and the center of the X-ray detector are coincident with each other without executing preliminary exposure, and there is an effect that image quality can be enhanced and a measurement time can be shortened.

DESCRIPTION OF REFERENCE NUMERALS

Figure 1:
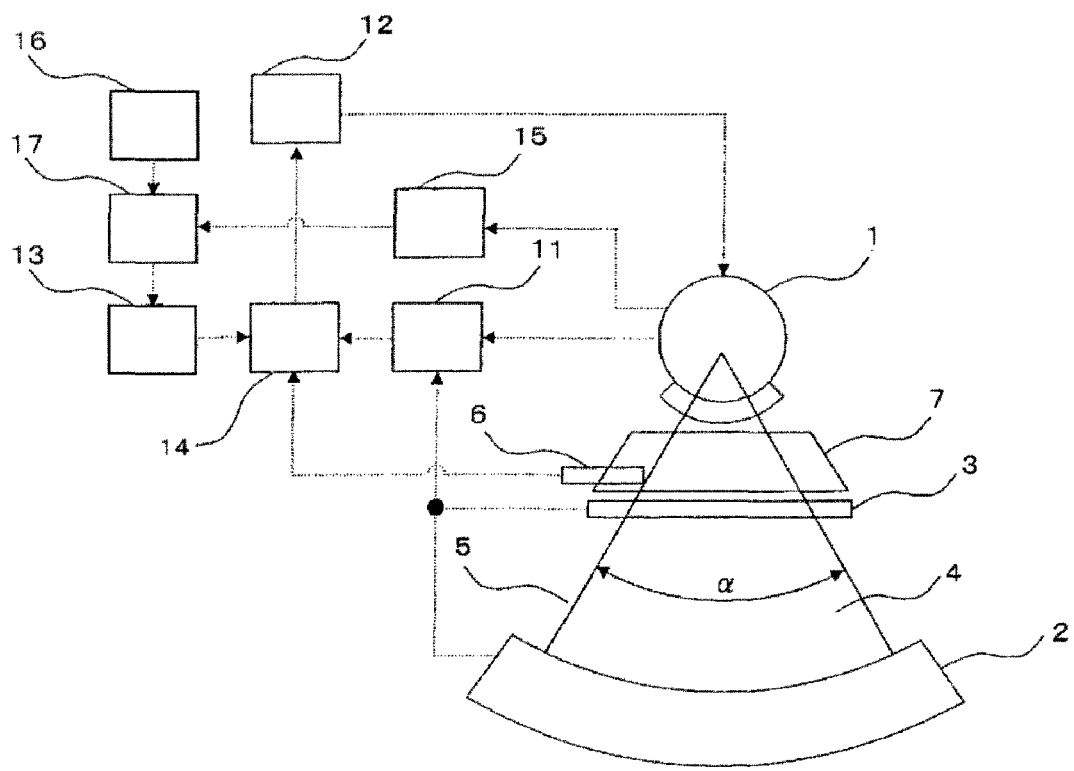
FIG. 1 is a diagram showing an example of the construction of an X-ray CT apparatus according to the present invention.

1 X-ray tube, 2 multi-channel X-ray detector, 3 collimator, 4 fan beam X-ray, 5 shift dedicated X-ray beam, shift detector, 7 support mechanism, 11 X-ray beam position detector, 12 driving controller, 13 storage device, 14 position controller, 15 accumulated heat capacity detector, 16 record storage unit, 17 focal point shift amount determining unit

BEST MODE FOR CARRYING OUT THE INVENTION

An embodiment of the present invention will be described hereunder with reference to FIG. 1.

An X-ray tube 1 emits an electron beam from the cathode (not shown) to the anode to discharge X-ray from the surface of the anode as a target. The X-ray tube 1 is supported on a scanner (not shown) by a support mechanism 7. A collimator 3 shapes corn-beam type X-ray discharged from the X-ray tube 1 into fan-beam type X-ray 4. The collimator 3 is formed so as to obtain X-ray having a slice thickness, that is, multi-slice (containing one slice thickness) X-ray, so that the fan-beam X-ray 4 having this multi-slice width is output at the output side of the collimator 3. A multi-channel X-ray detector 2 for measuring an examinee is provided at the confronting side to the X-ray tube 1 and the collimator 3. The detector 2 itself has an X-ray responsive area width (containing a multi-slice channel) corresponding to the slice thickness in accordance with the multi-slice width. A shift detector 6 or the multi-channel X-ray detector 2 for measuring the examinee is used to detect the X-ray beam position.

The shift detector 6 detects the shift of the focal point in the slice direction, and the X-ray detector 2 detects the shift of the focal point in the channel direction in an end portion sensitive area thereof. The focal point shift of the X-ray tube occurs in both the slice direction and the channel direction, and thus both the shifts are detected by both the detectors 2 and 6.

The focal point shift in the slice direction will be mainly described below. This is because the focal point shift in the slice direction is a main factor causing occurrence of artifact and thus the shift correction thereof is extremely important.

Important elements in this embodiment are a tube temperature detector (for example, temperature gauge) 15, a measurement condition (scan condition) record storage unit 16, a present accumulated heat capacity determining unit 17, and a storage device 13. The tube temperature detector 15 detects the temperature of the X-ray tube (the temperature of the anode or the like). The storage unit 16 stores, as a record, an X-ray exposure section T1, an X-ray stop section T2 (FIG. 2(c)), a tube voltage V, tube current I, etc. which are measurement condition parameters. On the basis of the temperature detected by the tube temperature detector 15 and the record of the measurement condition parameters stored in the storage unit 16, the determining unit 17 determines the present accumulated heat capacity (the detection value itself of the tube temperature detector 15 or a conversion value as a heat capacity value which corresponds to the detection value) and the present situation that the state is shifted to heating state or cooling state. For example, two focal point shift amounts P1 and P2 corresponding to the accumulated heat capacity Q1 in FIG. 2(a) described later are stored in the storage device 13. On the basis of the present situation of the determining unit 17, read-out of any one of the focal point shift amounts P1 and P2 or read-out of the addition value between the origin of the focal point and the shift amount of the focal point is performed from the storage device 13. The shift amount P1 or P2 is transmitted to a correcting processor 14.

When the device is subject to measurement preparation, X-ray beam position set information (the above shift amount or the addition value) read out from the storage device 13 in which the accumulated heat capacity and the focal point shift amount data obtained in advance are stored is transmitted to the correcting processor 14. Furthermore, position information of the X-ray tube 1, the shift detector 6 and the support mechanism 7 is converted to an electrical signal in an X-ray beam position detector 11, and transmitted to the correcting processor 14. The correcting processor 14 calculates a correction amount for the X-ray beam position on the basis of the electrical signal and the beam position set information from the storage device 13, and transmits the calculated correction amount and an operation instruction to a driving controller 12, thereby correcting the X-ray beam position.

Figure 2:
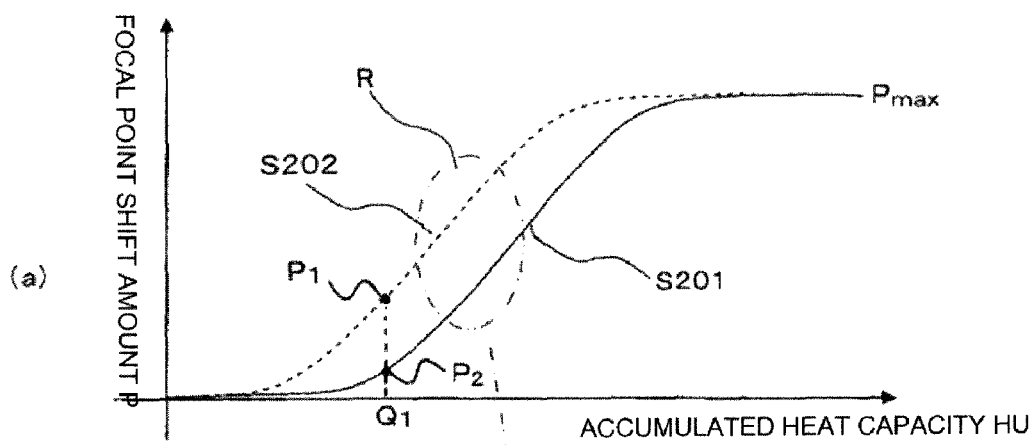
FIG. 2 is a diagram showing the relationship between an accumulated heat capacity and a focal point shift amount under heating/cooling operation of an X-ray tube according to the present invention.
Figure 2:
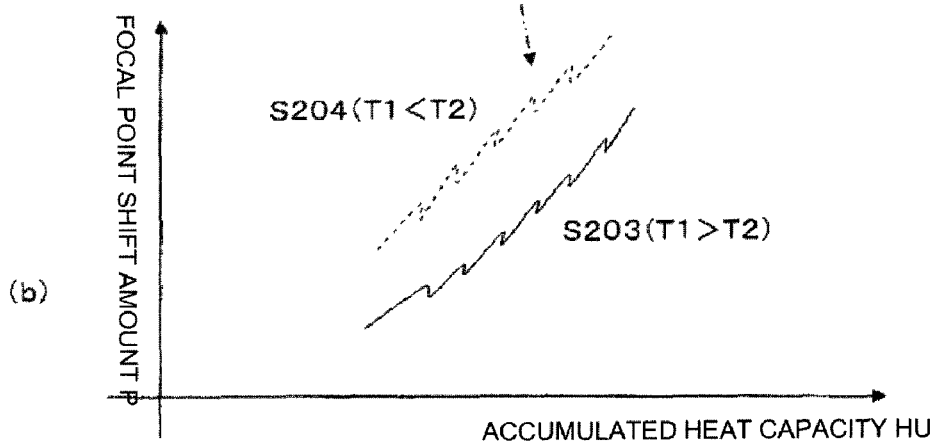
Figure 2:
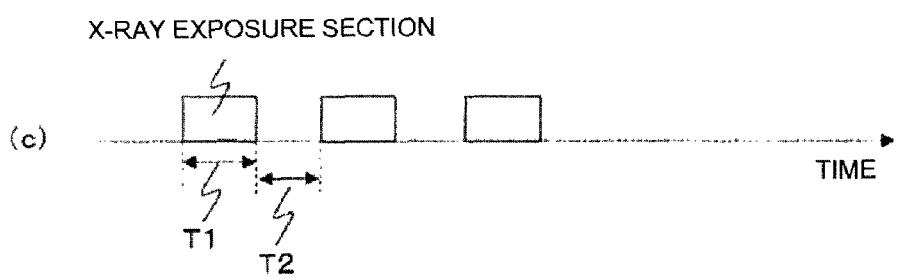

FIG. 2 shows an example of the focal shift amount data of each accumulated heat capacity under heating/cooling of the X-ray tube. S201 represents an example of the focal point shift amount in a process during which the X-ray tube is heated. S202 represents an example of the focal point shift amount in a process during which the X-ray tube is cooled.

The heat capacity of the X-ray tube is a numerical value representing heating of X-ray, and it is normally called as HU (heat unit). The heat capacity HU is represented as follows.

$$HU = t \cdot V \cdot I \qquad \{\text{Mathematical Expression 1}\}$$

Here, t represents X-ray radiation time width (X-ray exposure time width), V represents a tube voltage and I represents tube current. The product of these three measurement condition parameters is equal to the heat capacity HU.

The mathematical expression 1 is associated to the one exposure of X-ray, however, the heat quantity is actually continued to be accumulated in the X-ray tube due to repetitive exposure of X-ray. Therefore, the accumulated heat capacity must be considered in the above transition. There are both cases where accumulation of heat quantity causes increase of the accumulated heat capacity and where the accumulated heat capacity is reduced by heat radiation or forced cooling. Accordingly, the accumulated heat capacity repeats increase/decrease by heating and cooling. When the accumulated heat capacity increases to a high numerical value, the focal point shift amount increases. When the accumulated heat capacity decreases to a low numerical value, the focal point shift amount decreases.

In order to perform the shift correction, it is indispensable to numerically grasp the relationship between the accumulated heat capacity and the focal point shift amount as described above.

FIG. 2(a) shows a graph representing that the accumulated heat capacity HU and the focal point shift amount P have hysteresis relation like S201(heating)→S202(cooling) due to heating and cooling. This relational graph has been experimentally confirmed by the applicant and the inventor of this application.

Establishment of hysteresis relation indicates that record of heating and record of cooling must be considered and it would be impossible to determine an accurate focal point shift amount unless it can be identified whether an absolute accumulated heat capacity is under heating cycle or under cooling cycle although the absolute accumulated heat capacity is known by detection or on a mathematical expression.

For simplification, there is assumed a case where heat radiation of the X-ray tube is caused by natural heat radiation and X-ray exposure and non-exposure are repeated as shown in FIG. 2(c).

Under this case, an X-ray exposure section T1 and an X-ray stop (non-exposure) section T2 represent a heating state and a radiating state, respectively. Therefore, one cycle is formed by T1 and T2, and the following can be regarded as being satisfied under one cycle as follows:

for T1>T2, heating
for T1<T2, heat-radiating (cooling)

For T1>T2, heating progresses by repeating the cycle, and for T1<T2, cooling progresses by repeating the cycle.

Furthermore, the way how the heating quantity increases is varied in accordance with the magnitude of the values of V and I because the heat capacity is determined by the X-ray exposure section T1, the tube voltage V and the tube current I.

Past measurement conditions (sequence record data containing T1, T2, V, I, cycle frequency, etc.) of the X-ray tube until now as described above are stored as a record, whereby it can be determined whether the present condition progresses to the heating direction or the cooling direction. For example, the two shift amounts P1 and P2 are determined for the determined accumulated heat capacity Q1 from FIG. 2(a). However, by checking the past record, the focal point shift amount can be determined as P2 in the case of the heating direction or as P1 in the case of the cooling direction. The past means immediately previous past under which heat influence may exist. If the present condition returns to a normal state before heating, no past record before that time would be necessary, and the process is newly started and a new measurement condition is taken in as a record. Furthermore, consideration is also taken from the using frequency of the X-ray tube.

FIG. 2 will be described in more detail.

In FIG. 2(a), the focal point shift amount P reaches a mechanically settled limit value Pmax as the accumulated heat capacity increases, and then it is saturated. On the other hand, the focal point shift amount P approaches to zero as the accumulated heat capacity decreases.

FIG. 2(b) is an enlarged view of a site R shown in FIG. 2(a). FIG. 2(b) is a diagram showing micro variation of the shift amount under T1 and T2 as shown in FIG. 2(c). There is found such a tendency that heating increase occurs due to existence of the section T1 and cooling occurs due to existence of the section T2. Microscopically, a curve has a tendency of varying zigzag, however, there is no problem that it is treated as a continuous characteristic as shown in FIG. 2(a) in point of control.

The above case is an example based on natural heat radiation. However, even in a case where forced cooling means having air blowing means or the like is provided, the same consideration can be taken by adding a condition that a cooling effect appears strongly or the effect thereof remains even under heating.

The storage device 13 of FIG. 1 has the relationship between the accumulated heat capacity HU and the focal point shift amount P as data.

Figure 3:
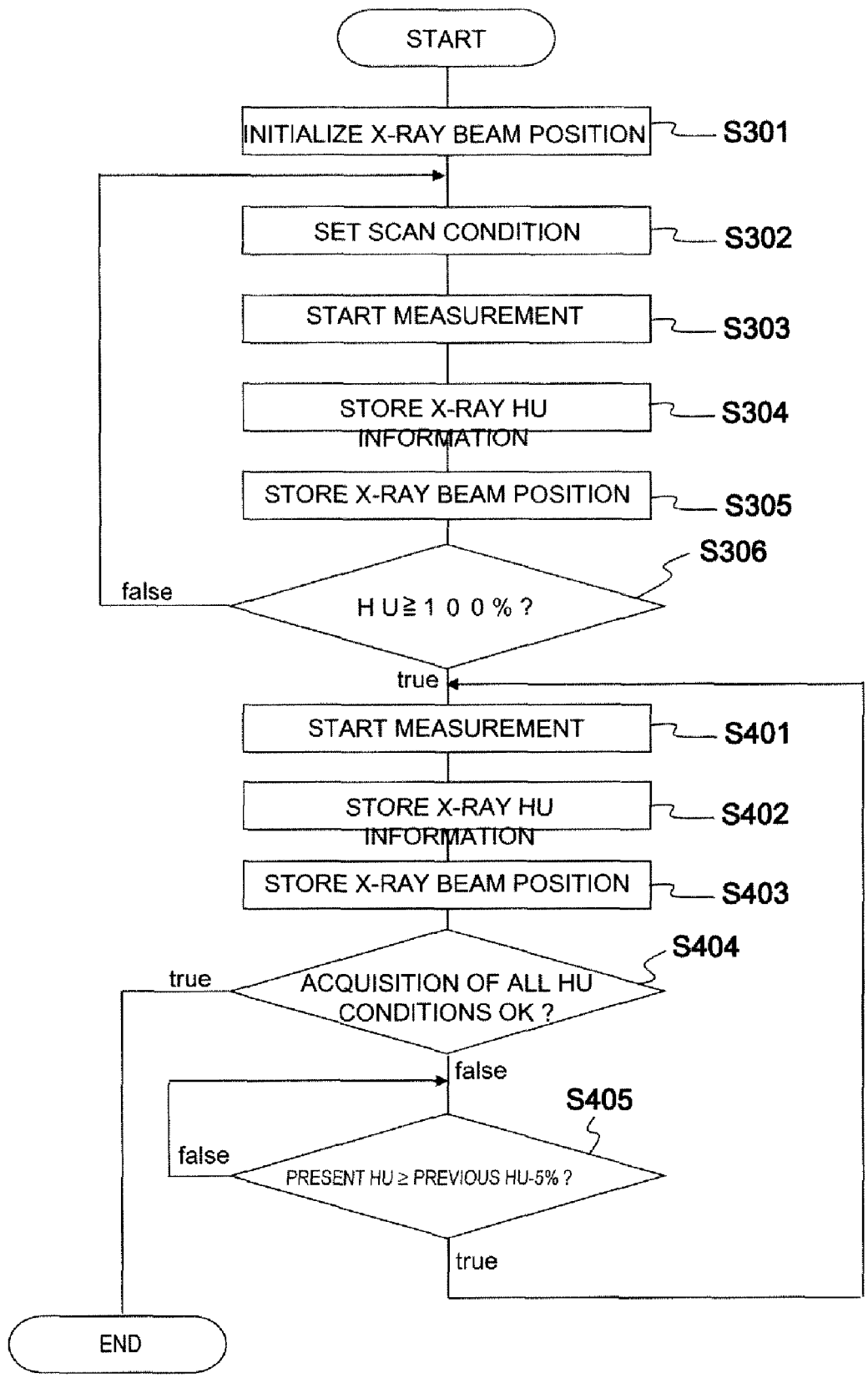
FIG. 3 is a flowchart showing X-ray beam correction data measuring processing under accumulated heat capacity heating/cooling operation according to the present invention.

FIG. 3 is a flowchart for obtaining physical characteristic data of the focal point shift amount and the accumulated heat capacity under heating/cooling of the X-ray tube. Steps S301 to S306 correspond to the flowchart for obtaining data under heating, and Steps S401 to S405 correspond to the flowchart for obtaining data under cooling. When data are obtained, during the period from S301 till S306 as indicated by S203 of FIG. 2, a characteristic as indicated by S201 of FIG. 2 is obtained by setting the X-ray exposure time period T1 and the interval time T2 till the next exposure to T1>T2, and during the period from S401 till S405, a characteristic as indicated by S204 of FIG. 2 is obtained by setting T1<T2.

In S301, the center of the X-ray beam and the center of the multi-channel X-ray detector are aligned with each other. Subsequently, an X-ray condition under scanning is set in S302. Here, the setting of the X-ray condition means the setting of (1) tube voltage, (2) tube current and (3) scan time out of the settable conditions under scanning. Subsequently, exposure of X-ray is performed in S303, accumulated heat capacity information under exposure is obtained in S304, and the X-ray beam position (up accumulated heat capacity data) is obtained in S305. Thereafter, in S306, it is determined whether the rate of the accumulated heat capacity to the heat capacity of the X-ray tube is less than 100% or equal to 100%. When the rate is less than 100%, the exposure of X-ray is subsequently performed to obtain accumulated heat capacity and position information data. When the rate is equal to 100%, the measurement is finished, and the obtained data are stored in the storage device 13. Subsequently, the characteristic data of the focal point shift amount and the accumulated heat capacity under cooling are obtained.

The exposure of X-ray is performed in S401 to obtain accumulated heat capacity information under the exposure in S402 and obtain the X-ray beam position (dn accumulated heat capacity data) in S403. It is checked in S404 whether the X-ray beam position data in all the accumulated heat capacities are acquired or not. When the acquisition is not finished, the processing waits for cooling of the accumulated heat capacity in S405, and the step of S401 and subsequent steps are repeated at the time point when the accumulated heat capacity reaches an accumulated heat capacity which is required to be obtained. When accumulated heat capacity information and the X-ray beam position (dn accumulated heat capacity data) until the acquisition of all the data is completed and the accumulated heat capacity decreases from 100% till 0% are stored in the storage device 13.

Figure 4:
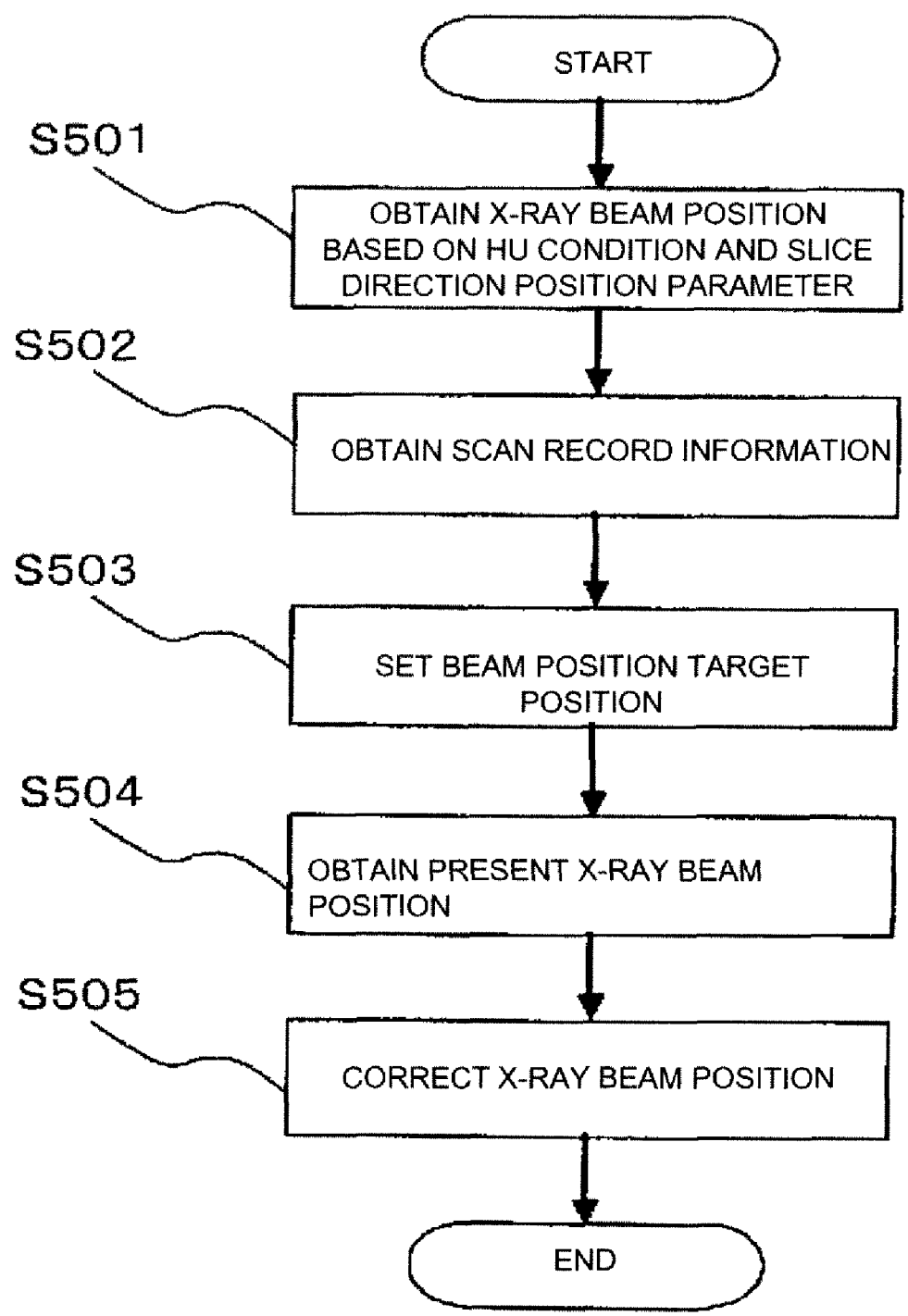
FIG. 4 is a flowchart of correction processing according to the present invention.

FIG. 4 is a flowchart showing the processing of executing correction by using scan record information when the next scan is started. In S501, beam position parameters are set by obtaining the up accumulated heat capacity data stored in the storage device 13 in advance, the do accumulated heat capacity data and the present accumulated heat capacity information. In S502, variation of the past accumulated heat capacity is obtained from the scan record information, and it is determined whether the accumulated heat capacity at the present time point (1) increases as indicated by S201 of FIG. 2 or (2) decreases as indicated by S202 of FIG. 2. The X-ray beam position for scanning to be next executed in S503 is set on the basis of the parameters obtained in S501 and the information as to whether the accumulated heat capacity obtained in S502 increases or decreases. Thereafter, after the present X-ray beam position is obtained in S504, and then X-ray beam is moved to the position concerned by the position control of the X-ray beam shift correcting function in S505. After the X-ray beam position correction is finished, the measurement preparation is completed, and the scan measurement is executed.

The X-ray beam position correction described here represents the control for shifting the X-ray beam to the center of the detector by means of moving the X-ray tube, means of moving the collimator or means of moving the detector. Furthermore, other means of deflecting the X-ray beam by magnetic field or the like may be used.

Furthermore, the X-ray beam position correction can be performed without exposure of X-ray, and thus optimum beam position correction can be performed on a real-time basis on the basis of the scan record and the present accumulated heat capacity information when the X-ray CT apparatus is in resting state, for example.

The invention claimed is:

1. An X-ray CT apparatus having an X-ray tube for generating X-ray with which an examinee is irradiated, and means for obtaining a tomographic image of the examinee by using a dose of transmitted X-ray collected by means for collecting X-ray transmitted through the examinee, characterized by comprising:

storage means for storing relationships between an accumulated heat capacity of the X-ray tube and a focal point shift amount in a slice direction;

accumulated heat capacity obtaining means for obtaining the accumulated heat capacity of the X-ray tube under heating and cooling, wherein the relationship between the accumulated heat capacity of the X-ray tube and the focal point shift amount in the slice direction obtained under heating is different than the relationship between the accumulated heat capacity of the X-ray tube and the focal point shift amount in the slice direction obtained under cooling;

determining means for determining which one of heating and cooling states the X-ray tube is under; and position correcting means for correcting the position of a slice direction of X-ray beam by using a focal point shift amount of the slice direction which is determined on the basis of the accumulated heat capacity obtained by the accumulated heat capacity obtaining means, a determination result of the determining means and the relationship stored in the storage means.

2. The X-ray CT apparatus according to claim 1, wherein the determining means determines heating/cooling on the basis of an exposure section and a stop section of X-ray.

3. The X-ray CT apparatus according to claim 2, wherein with respect to the relationship stored in the storage means, relationship under heating is obtained by repeating X-ray exposure under which the exposure section is longer than the stop section, and relationship under cooling is obtained by repeating X-ray exposure under which the exposure section is shorter than the stop section.

4. The X-ray CT apparatus according to claim 1, wherein the accumulated heat capacity obtaining means obtains a present accumulated heat capacity of the X-ray tube on the basis of an output of a temperature detector for detecting the temperature of the X-ray tube.

5. The X-ray CT apparatus according to claim 1, wherein the accumulated heat capacity obtaining means obtains a present accumulated heat capacity of the X-ray tube on the basis of X-ray exposure record of the X-ray tube.

6. An X-ray beam position correcting method for an X-ray CT apparatus having an X-ray tube for generating X-ray with which an examinee is irradiated, and means for obtaining a tomographic image of the examinee by using a dose of transmitted X-ray collected by means for collecting X-ray transmitted through the examinee, characterized by comprising:

a step of obtaining relationships between an accumulated heat capacity difference between heating and cooling of the X-ray tube and a focal point shift amount in a slice direction;

a step of obtaining the accumulated heat capacity of the X-ray tube under heating and cooling, wherein the relationship between the accumulated heat capacity of the X-ray tube and the focal point shift amount in the slice direction obtained under heating is different than the relationship between the accumulated heat capacity of the X-ray tube and the focal point shift amount in the slice direction obtained under cooling;

a step of determining which one of heating and cooling states the X-ray tube is under; and a step of correcting the position of a slice direction of X-ray beam by using a focal point shift amount of the slice direction which is determined on the basis of the accumulated heat capacity, the determination result and the relationship.

* * * * *